United States Patent [19]

Fujita et al.

[11] Patent Number: 5,031,127
[45] Date of Patent: Jul. 9, 1991

[54] MOLTEN INJECTION-MOLDING METHOD

[75] Inventors: Shigeru Fujita; Susumu Harada, both of Numazu, Japan

[73] Assignee: Toshiba Machine Co., Ltd., Tokyo, Japan

[21] Appl. No.: 272,792

[22] Filed: Nov. 18, 1988

[30] Foreign Application Priority Data

Nov. 27, 1987 [JP] Japan .................................. 62-297854
Nov. 27, 1987 [JP] Japan .................................. 62-297855
Nov. 27, 1987 [JP] Japan .................................. 62-297856

[51] Int. Cl.$^5$ ......................... G06F 15/31; G05D 7/06
[52] U.S. Cl. ..................... 364/476; 425/145; 364/578
[58] Field of Search ................ 364/476, 578, 754; 425/145

[56] References Cited

U.S. PATENT DOCUMENTS 4,326,255 4/1982 Fujita .................................. 364/476
4,787,057 11/1988 Hammond ........................... 364/754
4,797,842 1/1989 Nackman et al. .................... 364/578

OTHER PUBLICATIONS

"Flow Analysis Network (FAN)-A Method for Solving Flow Problems in Polymer Processing", *Polymer Engineering and Science*, Sep. 1974, vol. 14, No. 9, by Z. Tadmor et al., pp. 660-665.

Zienkiewicz: The Finite Element Method, 1977 McGraw Hill (Textbook), pp. 93/118.
Shephard: Finite Element Modeling within an Integrated Geometric Modeling Environment, Part I: Mesh Generation, pp. 61/71.

*Primary Examiner*—Felix D. Gruber
*Attorney, Agent, or Firm*—Young & Thompson

[57] ABSTRACT

A molten injection-molding method is applicable to any system of dividing a molded product form model into micro-elements and analyzing a molten material flow behavior within the mold by the use of numerical analytic techniques that include the finite element method, boundary element method, difference method, and FAN method, among others. First, the entire length of time required for the process of filling the mold with a molten material is divided into an arbitrary number of intervals, representing the filling progress in each individual time interval in an equitime curve diagram. This is followed by next not only deriving the distance segmented by each pair of adjacent equitime curves based on interrelations of the divided micro-element and equitime curves, but also computing the individual filling speeds, and then making a graphic display on display equipment of the variations in these filling speeds over an entire filling cycle, in order to evaluate, and find, the filling speeds at which an optimum mold filling cycle may be achieved.

11 Claims, 8 Drawing Sheets

| EQUITIME LINE LEVEL | |
|---|---|
| 1 | 5.000E-2 |
| 2 | 1.000E-1 |
| 3 | 1.500E-1 |
| 4 | 2.000E-1 |
| 5 | 2.500E-1 |
| 6 | 3.000E-1 |
| 7 | 3.500E-1 |
| 8 | 4.000E-1 |
| 9 | 4.500E-1 |
| 10 | 5.000E-1 |
| 11 | 5.500E-1 |
| 12 | 6.000E-1 |
| 13 | 6.500E-1 |
| 14 | 7.000E-1 |
| 15 | 7.500E-1 |
| 16 | 8.000E-1 |
| 17 | 8.500E-1 |
| 18 | 9.000E-1 |
| 19 | 9.500E-1 |
| 20 | 1.000E 0 |

MOLTEN INJECTION-MOLDING METHOD

FIELD OF THE INVENTION

This invention relates generally with methods to evaluate, and determine, optimum molding conditions for the output of high quality molded products when injection-molding plastic resin and other molten materials, and particularly with methods to judge the acceptability or otherwise of, and evaluate, a given filling speed by displaying variations along the passage of time in the filling speed for a molten material employed.

BACKGROUND OF THE INVENTION

In the conventional intra-mold molten resin flow analysis (simulation) for injection-molding a plastic resin material, an extensively employed approach has been used to divide a form model of the molded product into numerous micro-elements as shown in FIG. 1, and to compute their behavior by solving motional equations, continuity equations, and energy equations of the fluid by the use of a finite element method, boundary element method, difference method, and other numerical analytic techniques.

Under any such intra-mold molten resin flow analytical method, it is by inputting and computing the parameters of a resin selected and the molding operating conditions including a resin temperature, mold temperature, and filling speed, that a fill pattern (see FIG. 2) indicating the resin filling progress status (times) may be acquired through individually predesignated calculations.

None of the conventional resin flow analytical methods just discussed, however, incorporate any means to tell if the conditional input settings have been appropriate, look for even more appropriate input settings, or judge which of a number of sets of conceivable conditional input settings is best suited for purposes at hand. In consequence, empirical knowhow has had to be relied on that is acquired only through undertaking repeated comparative studies on analytical findings against actual moldings, in order to assess the validity of computed results.

Thus, the conventional intra-mold resin flow analytical method has been employed primarily for assessing the validity of physical configurations of a molded product (such as its wall thicknesses, gate locations and count, runner dimensions, etc.) by inputting the resin temperature, mold temperature, filling speed, and other parameters that have been gained in advance by empirical knowledge, and no attempts have yet been made to evaluate the appropriateness of molding conditions.

Nevertheless, the intra-mold resin flow analysis should originally address by programmed operations the task of judging molding feasibilities and degree of difficulty and deriving the requirements for producing a given molded product, at a stage when the product design is complete but before making its mold, and is demanded not only to assess the mold form-related appropriateness (of wall thicknesses, gate locations and count, gate and runner dimensions, etc.), but also to compute to derive appropriate molding condition ranges and optimum molding conditions. Ultimately, the determination of all the molding operating conditions is looked forward to of the resin flow analysis.

Accordingly, the objective of this invention is to provide a molten injection-molding material flow analysis evaluating method under which by utilizing the equitime curve diagrams of a conventional mold fill pattern for the molten material flow analysis over a given mold, and by deriving each individual filling speed from the distance between individual equitime curves, the speed variation behavior during a filling cycle may be displayed to enable evaluating, and assessing the appropriateness of, input filling speed settings.

SUMMARY OF THE INVENTION

The molten injection-molding material flow analysis evaluating method of this invention, when applied to any system of dividing a molded product form model into micro-elements and analyzing a molten material flow behavior within the mold by the use of numerical analytic techniques that include the finite element method, boundary element method, difference method, and FAN method, among others, is characterized by first dividing the entire length of time required for the process of filling the mold with a molten material into an arbitrary number of intervals, representing the filling progress in each individual time interval in an equitime curve diagram, next not only deriving the distance segmented by each pair of adjacent equitime curves based on interrelations of the divided micro-element and equitime curve, but also computing the individual filling speeds, and then making a graphic display on display equipment of the variations in these filling speeds over an entire filling cycle, in order to evaluate, and find, the filling speeds at which an optimum mold filling cycle may be achieved.

Said evaluating method may also be configured by first selectively setting an arbitrary point within any of the micro-elements of division, drawing a normal line to the equitime curve that corresponds to the micro-element through the point just set, finding the point of intersection between the normal line and the boundary of an adjacent element, next drawing a normal line to the equitime curve that corresponds to the adjacent element containing the point of intersection just found, finding another point of intersection between the normal line just drawn and the boundary with another adjacent element, then repeating the series of steps with that other adjacent element and still other adjacent elements further on, and generating a filling flow curve diagram by connecting together the intersecting points with said individual normal lines set on the boundaries of said individual elements, into one of its versions to not only acquire the lengths segmented by each pair of adjacent equitime curves on said filling flow curve diagram, but also compute individual filling speeds.

Another preferable version of said evaluating method may be configured by having said individual filling speeds computed through finding the points of intersection between said filling flow curves and individual equitime curves, and through using the linear distances between the intersecting points on each pair of adjacent equitime curves.

Still another version may be configured, when after finding the points of intersection between said normal lines and the boundary lines of each pair of adjacent element, a sharp angle is formed by the equitime curve of an element with which the next flow curve segment is to be plotted and said boundary line, by drawing a normal line to the equitime curve of each of the two elements that share said boundary line, and having a line that bisects an angle formed by the two normal lines find a point of intersection with the boundary line of another adjacent element.

A preferable alternative may be configured by simultaneously displaying a profile of filling speed input settings, or wall thickness variations at all the elements along a filling flow curve, or else temperature settings of the fixed and mobile plates of a mold at all the elements along a filling flow curve.

As another alternative, said evaluating method may also be configured to not only derive the mean distance between pairs of adjacent equitime curves from the area of zones each bordered by a pair of adjacent equitime curves and the mean overall length of the equitime curves, but also compute a mean filling speed from each mean distance.

A preferable version of the above may be configured by displaying not only the variations in individual filling speeds over an entire filling cycle as derived from the mean filling speed between each pair of adjacent equitime curves, but also a profile of input settings for the filling speed, simultaneously and while employing the same time axis for both the displays.

As an alternative, said evaluating method may also be configured to selectively set a point on any equitime curve that corresponds to any element, draw a normal line to the equitime curve from the point, both just set, next set a point of intersection between said normal line and an adjacent equitime curve, draw another normal line to this equitime curve, then repeat the series of steps with still other adjacent equitime curves further on, generate a filling flow curve diagram from the points set in correspondence with said equitime curves and the normal lines connecting them together, and not only derive the distance between each pair of adjacent equitime curves but also compute the individual filling speeds.

A preferable version of the above is to have a profile of filling speed input settings, or wall thickness variations at all the elements along a filling flow curve, or else temperature settings of the fixed and mobile plates of a mold at all the elements along a filling flow curve, displayed simultaneously.

Still another alternative of said evaluating method may be configured by first selectively setting on any equitime curve a point that corresponds to any element, drawing a normal line to the equitime curve just selected, another straight line that vertically intersects an adjacent equitime curve, and still another straight line that bisects an angle formed by the normal line and straight line just drawn, next setting a point of intersection between said bisecting line and adjacent equitime curve, drawing a bisecting line relative to the next adjacent equitime curve, then repeating the series of steps with still other adjacent equitime curves further on, to generate a filling flow curve diagram using the points set against said equitime curves and said bisecting lines that connect these points together, and not only deriving the length bordered by each pair of adjacent equitime curves of said filling flow curve diagram, but also computing the individual filling speeds.

In the above version, the straight line that vertically intersects said adjacent equitime curve may also be made to originate from an equitime curve contained within the element that includes within the intersecting point of a normal line to the adjacent equitime curve just mentioned from a point corresponding to said arbitrary element, or its extension.

In the above version, too, the simultaneous display on the same filling time axis as employed earlier for said filling flow curve diagram may preferably be made of a profile of the input filling speed settings, or wall thickness variations at all the elements along a filling flow curve, or else temperature settings of the fixed and mobile plates of a mold at all the elements along a filling flow curve.

When employing the molten injection-molding material flow analysis evaluating method, an equitime curve diagram that expresses the progress in filling the cavity-(ies) of a mold with a molten material may be utilized to generate a filling flow curve diagram based on the interrelation of individual adjacent elements and equitime curves, and thereby to represent on said equitime curve diagram a reference curve meeting predesignated criteria, and by deriving individual filling speeds from the distance between each pair of adjacent equitime curves along the filling flow curve and displaying the speeds over an entire filling cycle as individual filling speed variations on a display screen, filling speeds may readily be evaluated and judged with a view toward achieving optimum filling operations.

In addition, by utilizing said equitime curve diagram, deriving a mean filling speed from each pair of adjacent equitime curves, and displaying them as variations in the mean filling speed over an entire filling cycle, the evaluation and judgement of filling speeds for optimum even filling operations may be made simple to undertake.

In such cases as discussed above, a filling speed setting input profile may therefore be determined to lower any higher than prescribed speed or raise any lower speed by monitoring the individual filling speed variation between each pair of adjacent equitime curves.

Described below in depth by referring to attached drawings are some of the example embodiments of the molten injection-molding material flow analysis evaluating method under this invention.

PREFERRED EMBODIMENTS OF THE INVENTION

Figure 1:
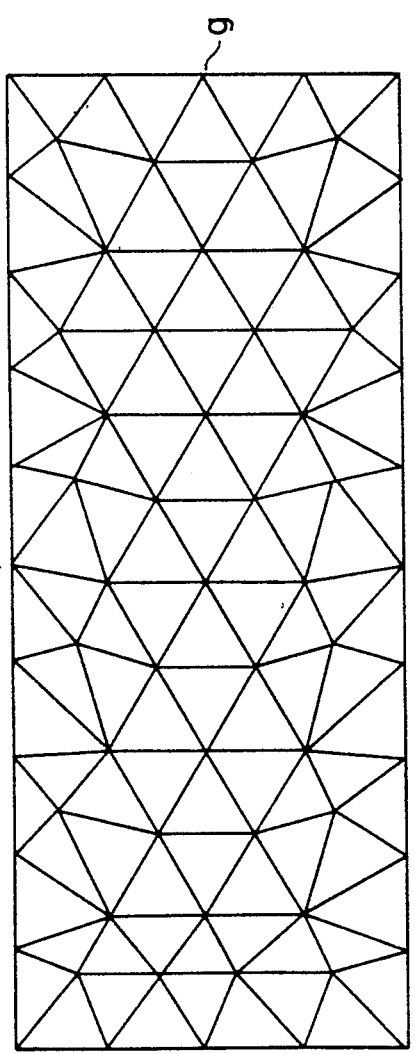
FIG. 1 graphically illustrates a product form model for injection-molding a molten material, that has been divided, or broken down, into 2-dimensional micro-elements.

The sequence of steps under this invention to analyze the intra-mold resin flow with regard to a given molded product form model is no different from that employed by the conventional simulation method. Specifically, as shown in FIG. 1, the molded product form model is divided into elements (that have been made triangular in the illustrated example but may just as well be made square or rectangular) for the intramold resin flow analysis, and the finite element method is applied to the elements. By making gate locations and quantity settings for the molded product form model and providing runners where required, form settings for the flow analysis may be made complete for the mold end.

Next, a plastic resin for use in molding is selected and its physical property data are input, after which a fill pattern indicating the advancing behavior of a mold-filling resin, or what is known as an equitime curve diagram (see FIG. 2), is duly analyzed. The steps up to this point are identical to those employed for the conventional intra-mold resin flow analysis.

EXAMPLE 1

Figure 2:
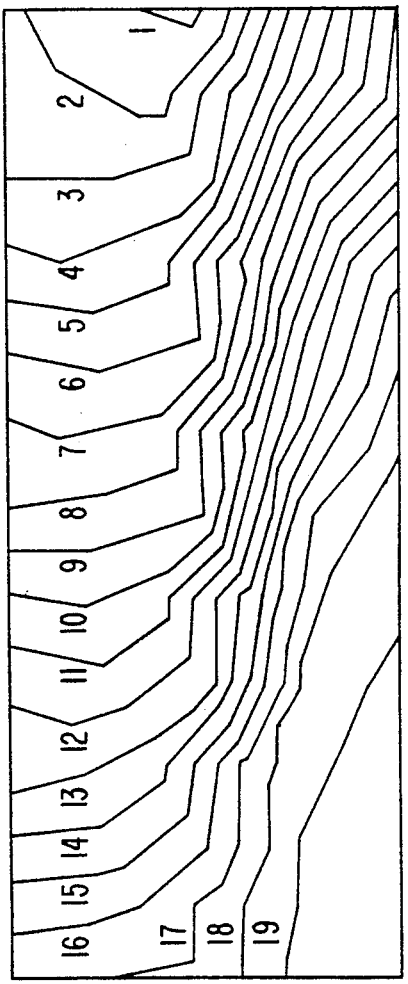
FIG. 2 shows the equitime curve diagram of a fill pattern for the form model shown in FIG. 1.
Figure 3:
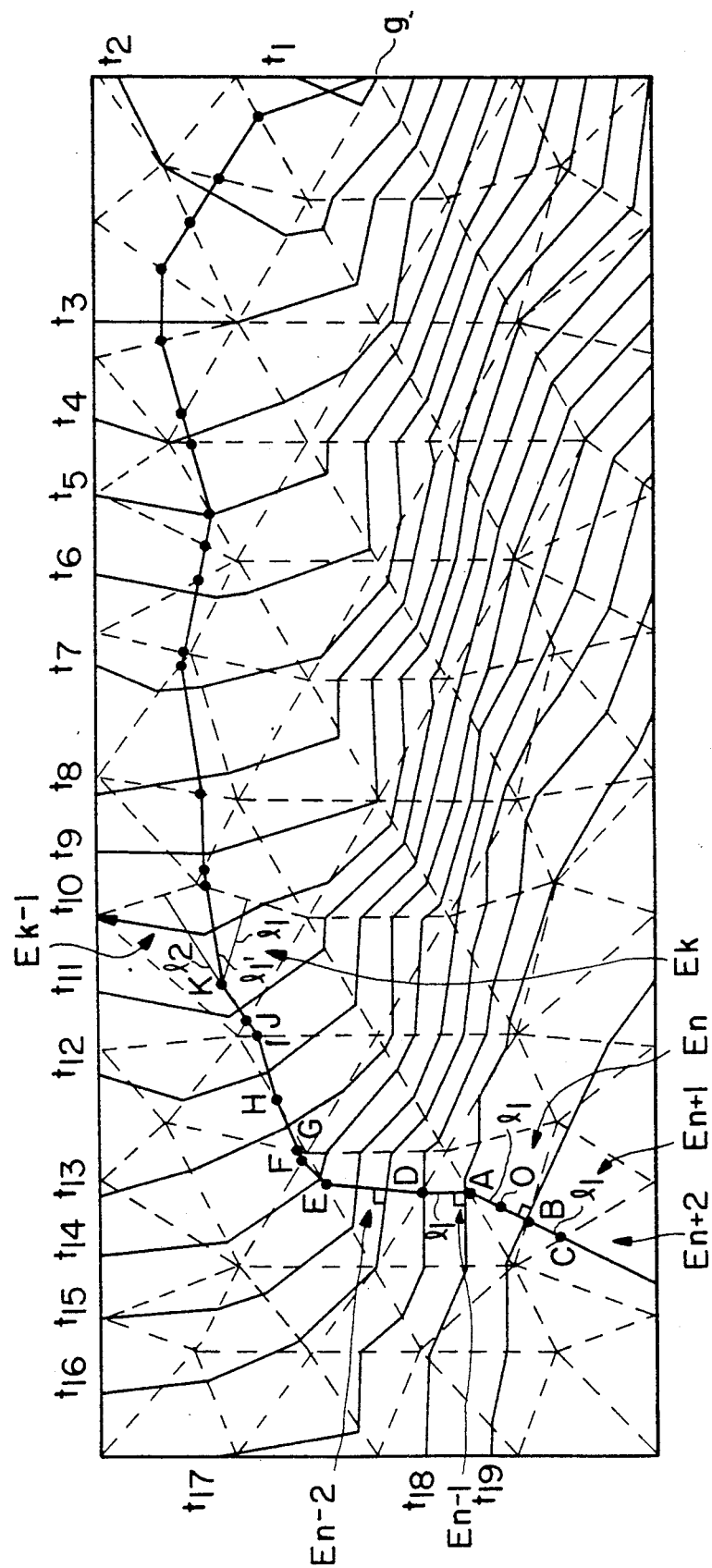
FIG. 3 shows an example embodiment of the molten injection-molding material flow analysis evaluating method under this invention, graphically illustrating a method to analyze the filling flow curve of a molten material.

For this example embodiment, a fill pattern diagram such as shown in FIG. 3 may be acquired by superimposing said element division illustrating diagram shown in FIG. 1 for the molded product form model over an equitime curve diagram serving as the fill pattern shown in FIG. 2.

In FIG. 3, characteristic response curves $t_1$ through $t_{19}$ represent the filling sequence indicating equitime flow fronts. Accordingly, where these equitime curves $t_1$ through $t_{19}$ are spaced evenly apart, variations in the filling speed may be held at a minimal level when filling the mold cavities with a material resin. A numerical representation of these filling time variations may be achieved by deriving the distance between, or spacing of, every pair of adjacent equitime curves.

Under this invention and by referring to FIG. 3 just discussed, first element $E_n$ is arbitrarily selected from among the elements into which the molded product form model has been divided or broken down, and point O again arbitrarily set within the element $E_n$ just selected. Next, line $l_1$ is drawn through point O just set normal to equitime curve $t_{19}$ that corresponds to element $E_n$, to find points A and B of intersection with the boundary lines of elements $E_{n-1}$ and $E_{n+1}$ that are adjacent to said element $E_n$. Then, originating from said intersecting point B, normal line $l_1$ to equitime curve $t_{19}$ is drawn for element $E_{n+}$, to find point of intersection C of the normal line $l_1$ with the boundary between its adjacent element $E_{n+1}$ and $E_{n-2}$, another element adjacent to $E_{n+1}$. In the other direction, line $l_1$ normal to equitime curve $t_{18}$ originating from said point of intersection A is drawn for element $E_{n-1}$, to find point of intersection D of the normal line $l_1$ with the boundary between its adjacent element $E_{n-1}$ and $E_{n-2}$, another element adjacent to $E_{n-1}$.

Thereafter, normal lines may continue to be drawn for other elements to equitime curves that correspond to adjacent elements, to find intersecting points E, F, G, H, I, J and K in that order on relevant inter-element boundaries.

In the example embodiment under discussion, when drawing a normal line originating from point of intersection K found on the boundary between adjacent elements $E_k$ and $E_{k-1}$, to equitime curve $t_{11}$ that corresponds to point K, the normal line to equitime curve $t_{11}$ corresponding to element $E_{k-1}$ will turn out to be $l_1$ which cannot be drawn within element $E_{k-1}$.

In a case such as the above, not only said normal line $l_1$ but also normal line $l_2$ to equitime curve $t_{11}$ for element $E_k$ are drawn, and a bisecting line $l'_1$ of the angle formed by the two normal lines is additionally drawn, to find point L of intersection with the boundary with either of the adjacent elements. Situations requiring this procedure occur when, as discussed with intersecting point K, the equitime curve that corresponds to an adjacent element about to be plotted for happens to be oriented only an angle below 90° away from its boundary. In other words, a normal line originating from point K referenced to the equitime curve of one of the adjacent elements is made as valid as another one drawn into the other adjacent element, so that the use of a line bisecting the angle between the two normal lines will serve to average the two valid normal lines out.

Figure 4:
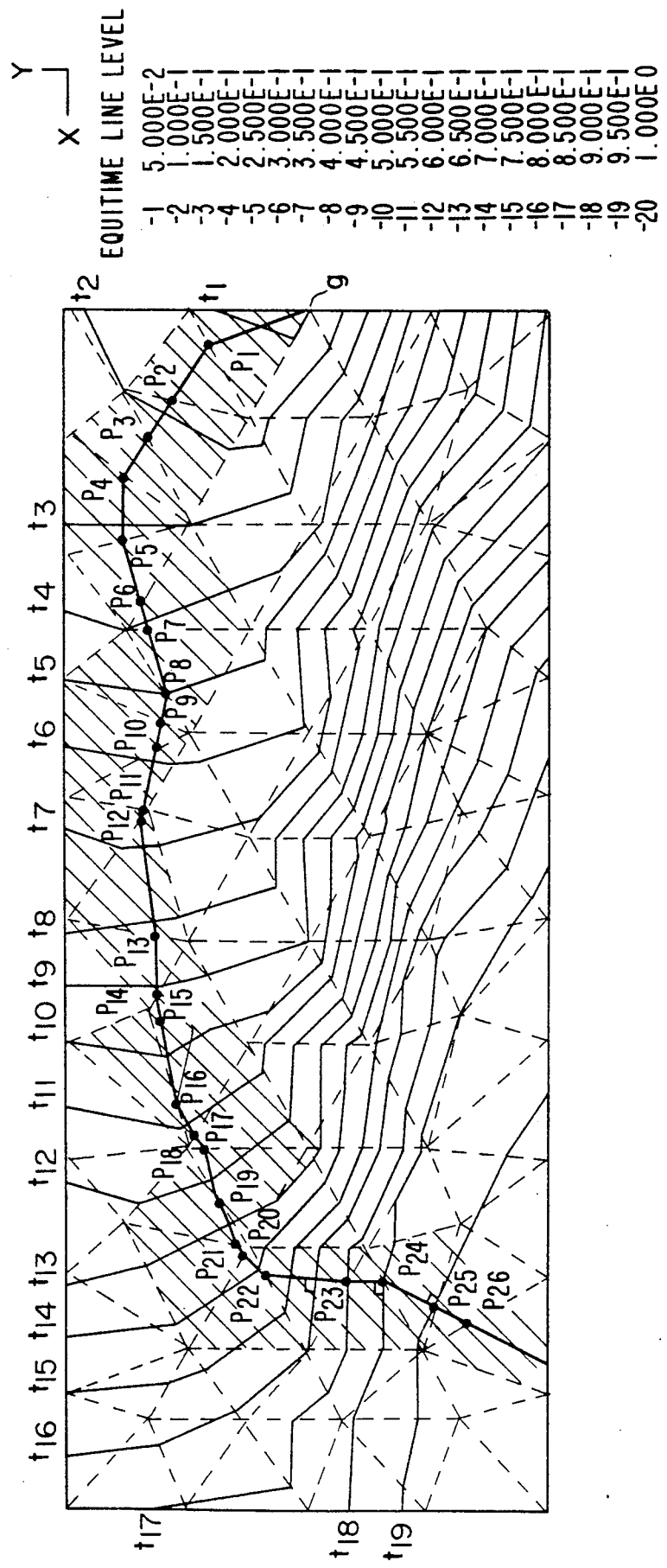
FIG. 4 graphically illustrates the breakdown into elements of a mold in conformance with an analytical process based on FIG. 3, its interrelations as a fill pattern with equitime curves, a filling flow curve, and a series of zones of the divided elements that correspond with said filling flow curve.

Thereafter, further intersecting points $P_1$ through $P_{26}$) may be set on adjacent element boundaries by following similar steps to the foregoing, and by connecting the points together with straight line segments, a single, continuous filling flow curve such as shown in FIG. 4 may be plotted. Incidentally, "g" in the diagram denotes a gate location.

Then by measuring parts of the filling flow curve each segmented by a pair of equitime curves, and dividing them individually with the times at which the equitime curves were set apart in the first place, their individual filling speeds $V_n$ may be derived.

Such filling speeds may be computed after finding points of intersection $P_1, P_2, \text{---}, P_{19}$ between the filling flow curve and individual equitime curves $t_1$ through $t_{19}$ (see FIG. 4), and measuring the distances between $P_1$ to $P_2$, $P_2$ to $P_3$, $\text{---}$, and $P_{18}$ to $P_{19}$.

Thus, filling speeds $V_1$ through $V_{19}$ against $t_1$ through $T_{19}$ shown in FIG. 4 may be derived.

Figure 5:
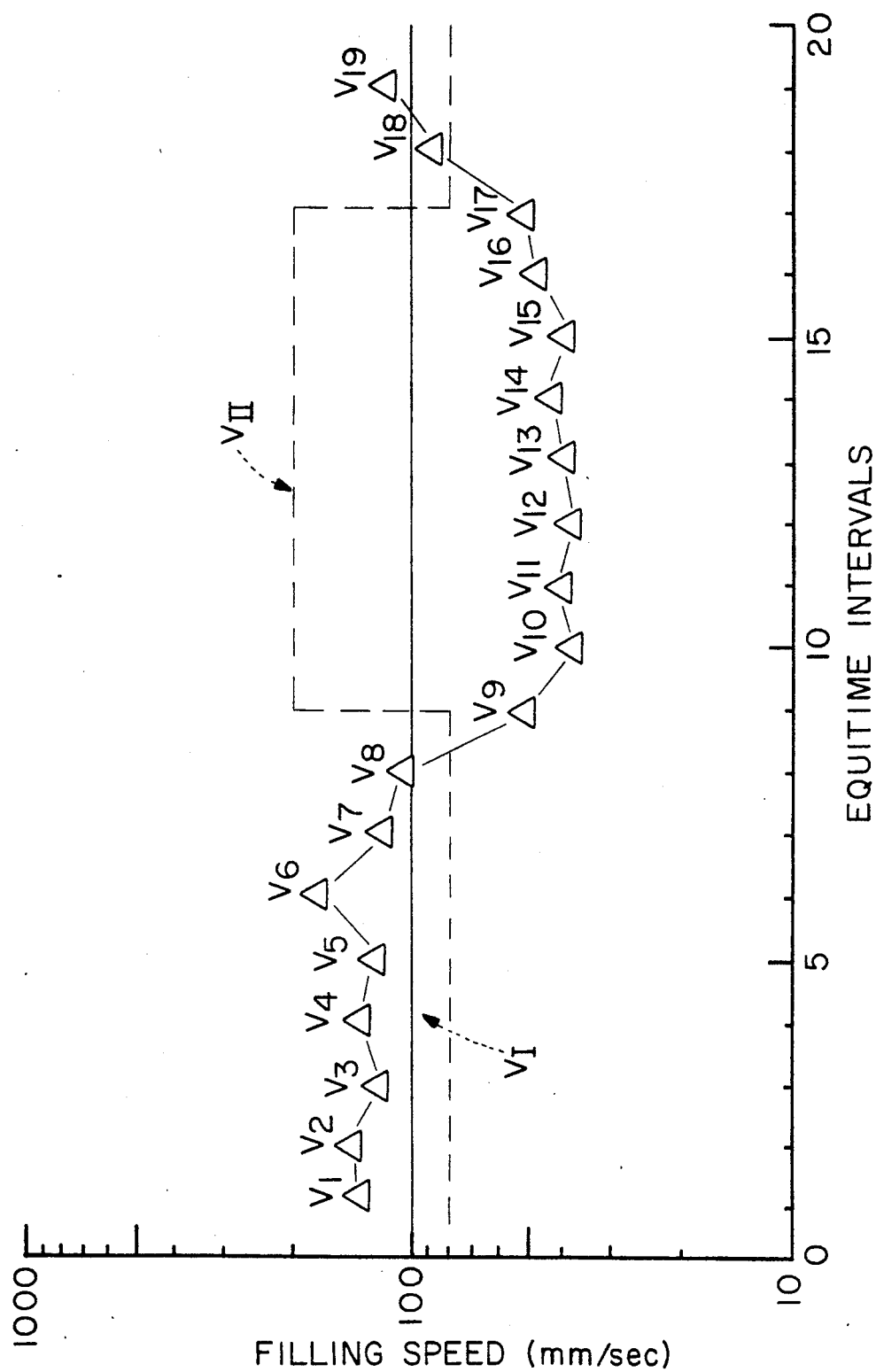
FIG. 5 shows a characteristic response curve of the filling speed to which the method of this invention has been applied.

The filling speed setting input profile employed for this example was $V_I$, and deviations therefrom due to the variation of filling speeds $v_1$ through $v_{19}$ between corresponding pairs of equitime curves may duly be computed as shown in FIG. 5.

As evident from the characteristic speed response curve shown in FIG. 5, the entire filling cycling of this example embodiment was executed under the input setting for a fixed speed indicated by $V_I$ but the actual filling speed is shown to have dropped down over equitime intervals 9 through 17. It is therefore possible to achieve an even speed filling behavior by employing the filling speed input setting $V_{II}$ indicated by a broken line in FIG. 5, to offset deviations from $V_I$ in the actual behavior indicated by a solid curve, in order notably to raise the speed over intervals 9 through 17.

Accordingly, by employing this invention and having the characteristic curve of FIG. 5 graphically displayed on a liquid crystal, CRT, plasma, EL, or similar other display unit, not only may the variations deviating from overall mean filling speed $V_I$ at individual equitime curves be readily evaluated and judged, but based on the deviations observed, an appropriately programmed filling speed setting input $V_{II}$ may also be formulated with ease.

In FIG. 5, only filling speed setting input profile $V_{II}$ has been shown superimposed over an ongoing actual filling speed plotting, but similar other displays may also be made with equal ease, such as wall thickness variations that indicate ongoing layer growths and temperatures at the fixed and mobile plates of a mold, both superimposed on divided elements over which the filling flow curve passes (a series of elements shown in FIG. 4 as a hatched zone), and enable the appropriateness of settings for molding to be judged in greater depth.

EXAMPLE 2

Figure 6:
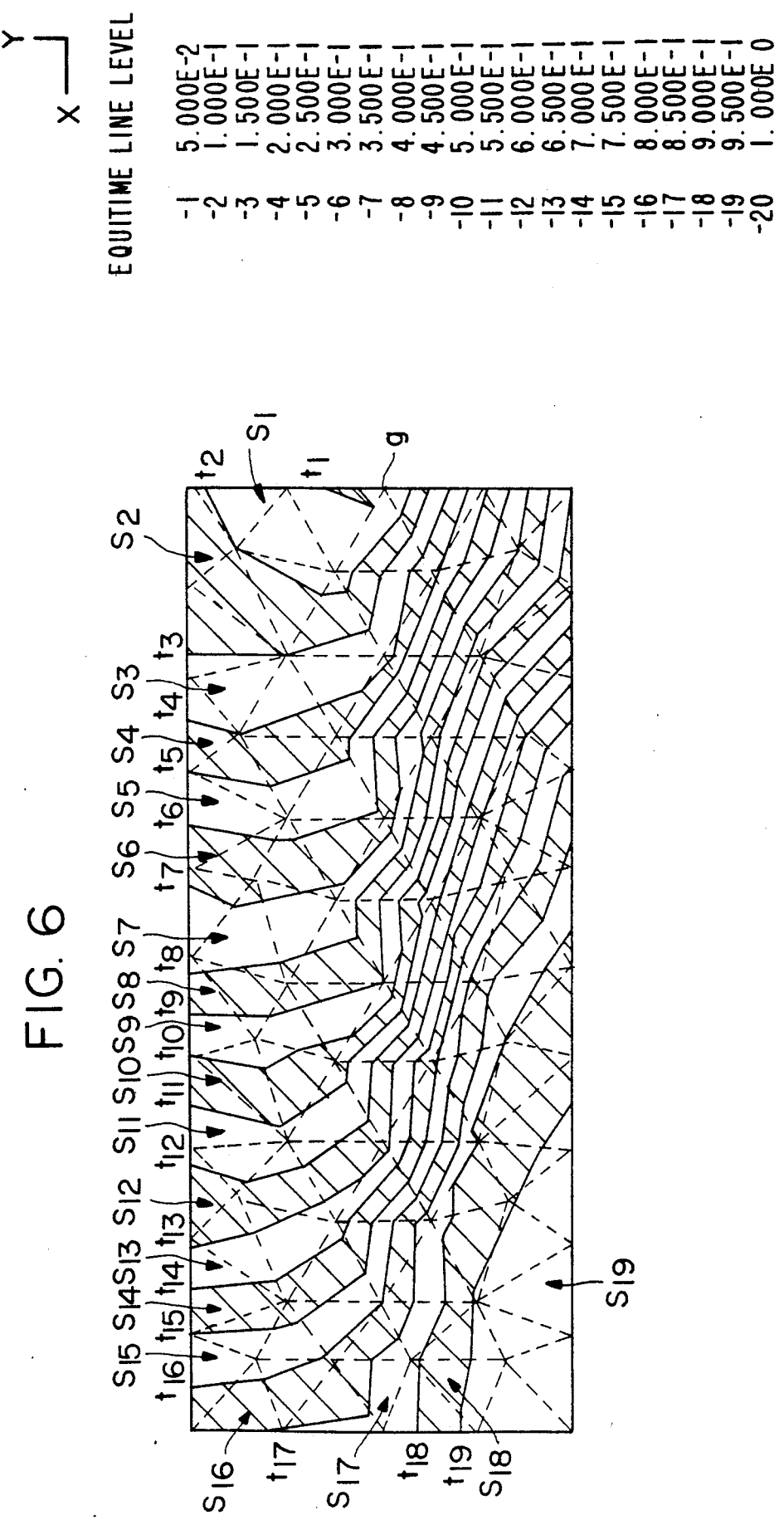
FIG. 6 graphically illustrates the element breakdown of a mold and its interrelations as a fill pattern with equitime curves, both of another example embodiment of the molten injection-molding material flow analysis evaluating method under this invention.

For this example embodiment, a fill pattern diagram such as shown in FIG. 6 may be acquired by superimposing the equitime curve diagram shown in FIG. 2 that serves as a fill pattern over the molded product form element breakdown diagram mentioned earlier and shown in FIG. 1. In FIG. 6, characteristic curves $t_1$ through $t_{19}$ represent equitime curves that indicate the sequence of filling. Accordingly, if these equitime curves $t_1$ through $t_{19}$ are spaced evenly apart, the filling of a mold with a resin may be achieved with minimal variations in the overall filling speed. To indicate these variations numerically, the mean value of spacings between every pair of adjacent equitime curves or the mean distance (or spacing) is derived.

For example, first, area $S_n$ ($=S_3$) of a zone bordered by two arbitrary equitime curves $t_n$ ($=t_2$) and $t_{n+1}$ ($=t_3$), and mean overall length $T_n$ of the individual equitime curves $t_n$ and $t_{n+1}$ ($=[t_n+t_{n+1}]/2$) are computed. Next, by using the computed result and calculating the value $S_n/T_n$, the mean distance (or spacing) of equitime curves $t_n$ and $t_{n+1}$ may be derived. Then, by dividing the mean distance with the time interval between $t_n$ and $t_{n+1}$, mean filling speed $V_n$ during the interval may be derived.

By repeating the above process, mean filling speeds $v_1$ through $v_{19}$ may similarly be derived for the equitime curves $t_1$ through $t_{19}$ shown in FIG. 6. The filling speed setting input profile employed for this example was $V_I$, and deviations therefrom due to the variation of mean filling speeds $v_1$ through $v_{19}$ in intervals between adjacent equitime curves may similarly be derived to those for the example embodiment 1 discussed earlier, as shown in FIG. 5.

Thus, in this example embodiment, too, not only may an even filling cycle be achieved by filling speed setting profile $V_{II}$ in view of the characteristic response curve shown in FIG. 5, in a manner similar to that employed for said example embodiment 1, but by graphically displaying said characteristic response curve, the variations deviating from overall mean filling speed $V_I$ at individual equitime curves may also be readily evaluated and judged, and based on the deviations observed, an appropriate filling speed setting input $V_{II}$ duly formulated as well with ease.

EXAMPLE 3

Figure 7:
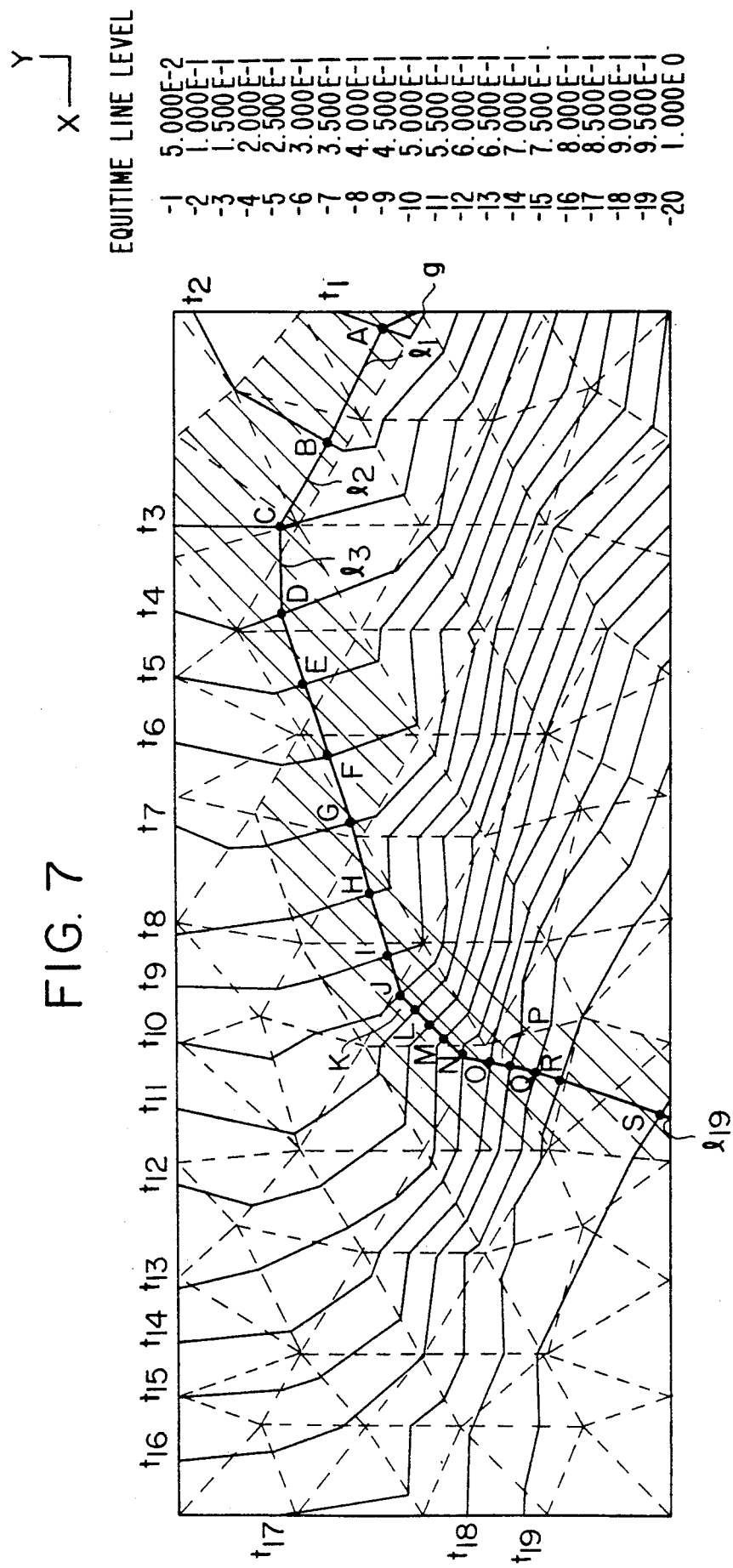
FIG. 7 graphically illustrates the element breakdown of a mold and its interrelations as a fill pattern with equitime curves, as well as a filling flow curve and a series of zones of the divided elements that correspond to said filling flow curve, all of still another example embodiment of the molten injection-molding material flow analysis evaluating method under this invention.

For this example embodiment, a fill pattern diagram such as shown in FIG. 3 may be acquired by superimposing said element division illustrating diagram shown in FIG. 1 for the molded product form model over an equitime curve diagram serving as the fill pattern shown in FIG. 7.

In FIG. 7, characteristic response curves $t_1$ through $t_{19}$ represent the filling sequence indicating equitime flow fronts. Accordingly, where these equitime curves $t_1$ through $t_{19}$ are spaced evenly apart, variations in the filling speed may be held at a minimal level when filling the mold cavities with a material resin. A numerical representation of these filling time variations may be achieved by deriving the distance between, or spacing of, every pair of adjacent equitime curves.

Under this invention and based on said FIG. 7, first an arbitrary point A is selected on the first equitime curve $t_1$ as counted from gate location g at which a filling resin enters, and said location g connected with point A with a straight line segment. Next, line $l_1$ is drawn normal to the first equitime curve $t_1$, originating from said point A, and its intersection with the second equitime curve $t_2$ assigned as point B. Then, line $l_2$ is drawn normal to the second equitime curve $t_2$, originating from said point B, and its intersection with the third equitime curve $t_3$ assigned as point C. Similarly, normal lines $l_3$ through $l_{19}$ are drawn to the third to nineteenth equitime curves $t_3$ through $t_{19}$, and by connecting the normal lines together with line segments, a single, continuous filling flow curve such as shown in FIG. 7 may be plotted.

Next, based on the thus acquired filling flow diagram, distances between each pair of adjacent points of intersection between individual filling flow and equitime curves, A to B, B to C, ---, and R to S, are derived, and by dividing these distances with the time spacing of each pair of adjacent equitime curves, a series of filling speeds $V_n$ may be derived. It is by this process that individual filling flow speeds $v_1$ through $v_{19}$ at $t_1$ through $t_{19}$ shown in FIG. 7 have been derived.

The filling speed setting input profile employed for this example embodiment was $V_I$, and deviations therefrom due to the variation of mean filling speeds $v_1$ through $v_{19}$ in intervals between adjacent equitime curves may similarly be derived to those of the example embodiment 1 discussed earlier, as shown in FIG. 5.

Thus, in this example embodiment, too, not only may an even filling cycle be achieved by filling speed setting profile $V_{II}$ in view of the characteristic response curve shown in FIG. 5, in a manner similar to that employed for said example embodiment 1, but by graphically displaying said characteristic response curve, the variations deviating from overall mean filling speed $V_I$ at individual equitime curves may also be readily evaluated and judged, and based on the deviations observed, an appropriate filling speed setting input $V_{II}$ duly formulated as well with ease.

For this example embodiment, over and above the display superimposed over an ongoing actual filling speed plotting of filling speed setting input profile $V_{II}$, wall thickness variations that indicate ongoing layer growths and temperatures at the fixed and mobile plates of a mold may also be displayed simultaneously and superimposed on elements over which the filling flow curve passes (a series of elements shown in FIG. 7 as a hatched zone).

EXAMPLE 4

Figure 8:
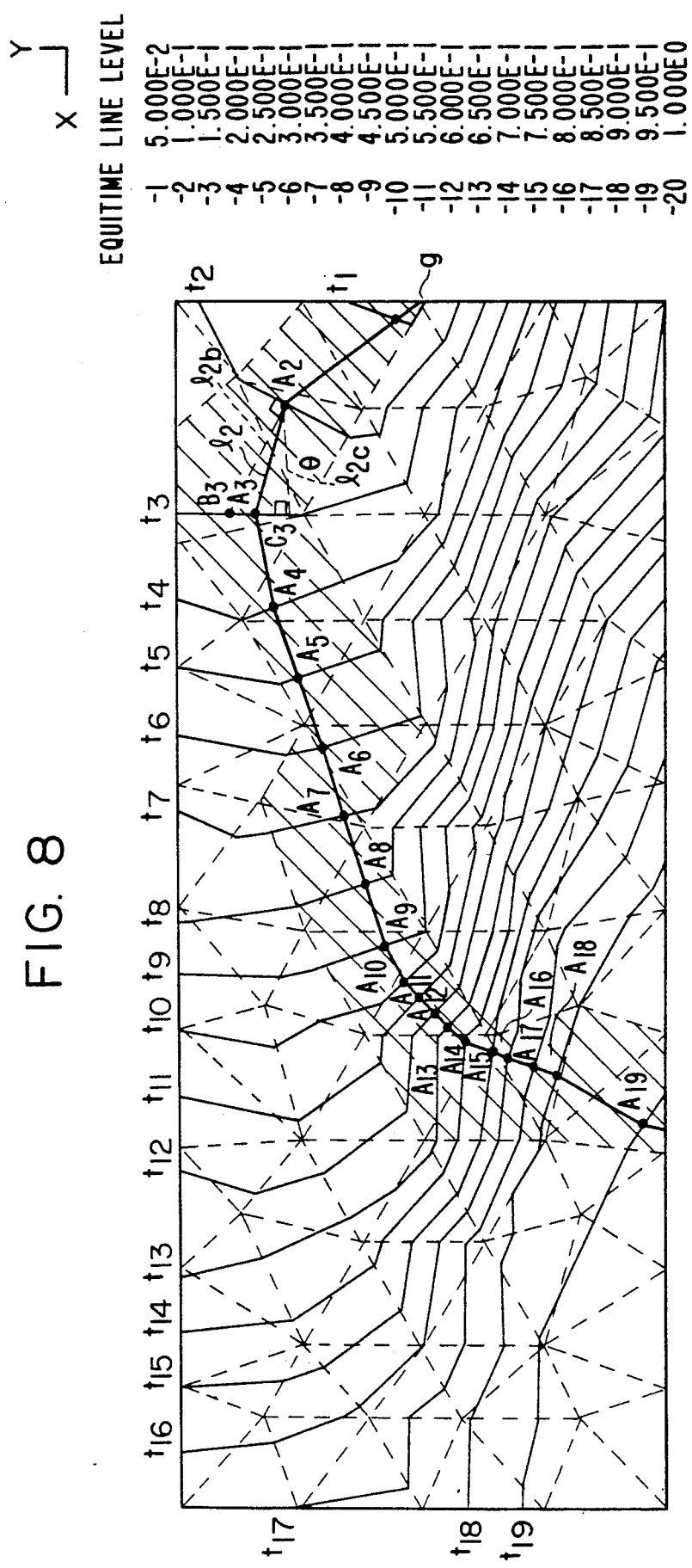
FIG. 8 graphically illustrates the element breakdown of a mold and its interrelations as a fill pattern with equitime curves, as well as a filling flow curve and a series of zones of the divided elements that correspond to said filling flow curve, all of a further example embodiment of the molten injection-molding material flow analysis evaluating method under this invention.
Figure 9:
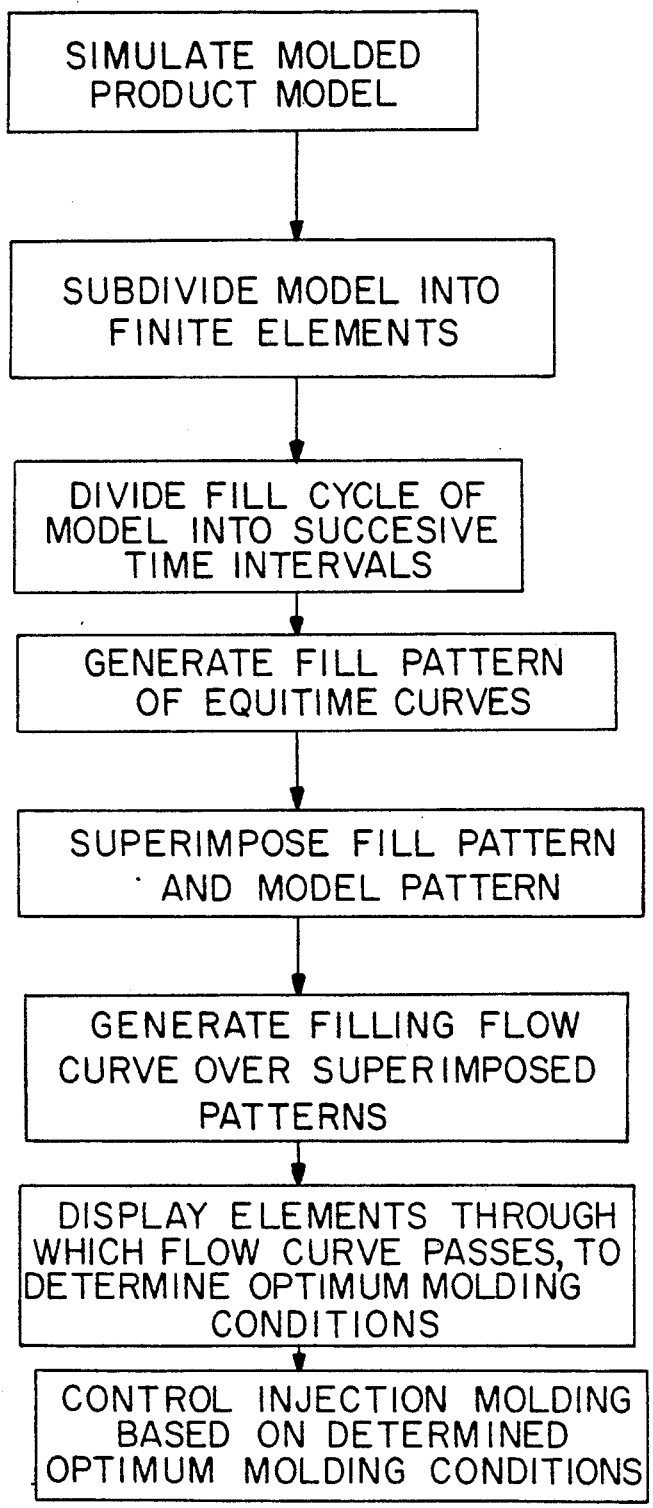
FIG. 9 is a flowchart schematically depicting the overall process according to the invention.

For this example embodiment, a fill pattern diagram such as shown in FIG. 8 may be acquired by superimposing the equitime curve diagram shown in FIG. 2 that serves as a fill pattern over the molded product form element breakdown diagram mentioned earlier and shown in FIG. 1. In FIG. 8, characteristic curves $t_1$ through $t_{19}$ represent equitime curves that indicate the sequence of filling. Accordingly, if these equitime curves $t_1$ through $t_{19}$ are spaced evenly apart, the filling of a mold with a resin may be achieved with minimal variations in the overall filling speed. To indicate these variations numerically, the mean value of specings between every pair of adjacent equitime curves or the mean distance (or spacing) is derived.

Under this invention and based on FIG. 8 mentioned above, first, equitime curve $t_n$ (the second equitime curve $t_2$ in the illustrated example) and point $A_n (=A_2)$ thereon are arbitrarily selected, and normal line $l_{nb} (=l_{2b})$ is drawn to said equitime curve $t_n (=t_2)$ originating from said point $A_n (=A_2)$ to intersect adjacent equitime curve $t_{n+1} (=t_3)$ at a point that will be assigned as $B_{n+1} (=B_3)$.

In addition, its point of intersection with straight line $l_{nc} (=l_{2c})$ that is normal to said adjacent equitime curve and passing through said point $A_n$ will be assigned as $C_{n+1} (=C_3)$. Now, its point of intersection with bisecting line $l_n (=l_3)$ of $\angle B_{n+1}/A_n/C_{n+1} (=\angle B_3/A_2/C_3)$ is looked for. The bisecting line $l_n$ at $\theta/2$ in angle has one half of the apex angle $\theta$ of a triangle formed by points $A_n$, $B_{n+1}$, and $C_{n+1}$ as its apexes, and serves to indicate the flow process of a resin from equitime curve $t_n$ to equitime curve $t_{n+1}$.

Thereafter, by similar steps, line segments bisecting the angles formed by normal lines $l_{nb}$ through $l_{19b}$ to equitime curves $t_n$ through $t_{19}$ passing through points $A_{n+1}$ through $A_n$, and straight lines vertically intersecting adjacent equitime curves $t_{n+1}$ through $t_{19}$ are drawn to reach points assigned as $A_{n+1}$ through $A_{19}$, and by connecting the line segments together, a single, continuous filling flow curve such as shown in FIG. 8 may be plotted. Incidentally, g denotes the location of a gate.

Further, based on the thus acquired filling flow curve, the distance between intersections of the individual filling flow and equitime curves, $A_1$ to $A_2$, $A_2$ to $A_3$, - - -, and $A_{18}$ to $A_{19}$, may be derived, and by dividing these distances with the equitime curve spacing time intervals, filling flow speeds $V_n$ at the equitime curves may be derived. It is by these steps that individual filling flow speeds $v_1$ through $v_{19}$ at $t_1$ through $t_{19}$ of the filling flow curve shown in FIG. 8 may be derived. The filling speed setting input profile employed was $V_I$ and the variations relative thereto of filling speeds $v_1$ through $v_{19}$ may be represented as shown in FIG. 5 in a manner similar to that for said example embodiment 1.

Thus, in this example embodiment, too, not only may an even filling cycle be achieved by filling speed setting probile $V_{II}$ in view of the characteristic response curve shown in FIG. 5, in a manner similar to that employed for said example embodiment 1, but by graphically displaying said characteristic response curve, the variations deviating from overall mean filling speed $V_I$ at individual equitime curves may also be readily evaluated and judged, and based on the deviations observed, an appropriate filling speed setting input $V_{II}$ duly formulated as well with ease.

For this example embodiment, too, over and above the display superimposed over an ongoing actual filling speed plotting of filling speed setting input profile $V_{II}$, wall thickness variations that indicate ongoing layer growths and temperatures at the fixed and mobile plates of a mold may also be displayed simultaneously and superimposed on elements over which the filling flow curve passes (a series of elements shown in FIG. 8 as a hatched zone).

As revealed by the example embodiments presented so far, this invention enables, for the flow analysis when filling the mold of a given form model with a molten resin, not only deriving individual filling speeds during the time interval between each pair of adjacent equitime curves, via an equitime curve diagram that indicates the mold fill pattern and a filling flow diagram derived therefrom, but also the filling speed variations over an entire filling cycle, and enables evaluating and judging the appropriateness of any fill pattern employed, with ease.

In addition, the invention further enables, based on an equitime curve diagram that represents said fill pattern, deriving not only the mean filling speed during time intervals between each pair of adjacent equitime curves, but also the filling speed variations over an entire filling cycle, and therethrough, evaluating or judging the appropriateness of any fill pattern with ease.

Furthermore, the invention also enables appropriately programmed filling speed settings to be made for an even filling cycle, based on such filling speed variations as the above during the time interval between each pair of adjacent equitime curves.

Accordingly, by employing this invention for the flow analysis of a resin over a molded product form model, not only may appropriateness of the conditions to output high quality molded products be judged with ease by means of a simple graphic display, but based on the judgement outcome, a variety of molding conditions may also be selected to achieve optimum settings, making outstanding contributions to the generation of superior programs for the injection-molding of any molten plastic resin.

Although in the example embodiments presented so far, the injection molding method has been discussed in depth, this invention is not limited by such embodiments, but may also be applied to the injection molding of any other molten material than resins, such as for example to diecasting equipment, and may of course be modified for various other applications as well, as long as within the time scope and spirit of this invention.

What is claimed is:

1. A method for injection molding a product, comprising the steps of:
   (a) simulating an injection-molded product formed in a mold filled at a filling speed during a fill cycle with molten material by forming a model of the product;
   (b) generating a model pattern of the model by subdividing the model into a plurality of elements;
   (c) dividing the fill cycle into a plurality of successive time intervals;
   (d) generating a fill pattern of equitime curves, each representative of the advancement over time of the molten material through the mold for respective successive time intervals;
   (e) superimposing the fill pattern over the model pattern;

(f) generating from the superimposed patterns on individual filling speed for each time interval;

(g) visually displaying the individual filling speed over the fill cycle to determine optimum filling speed conditions; and (h) controlling an injection molding operation in accordance with the determined optimum filling speed conditions.

2. The method according to claim 1, wherein step (b) is performed by forming each element with linear boundary lines, and wherein step (d) is performed by forming each equitime curve with linear segments.

3. The method according to claim 1, wherein step (f) is performed by generating a filling flow curve over the superimposed patterns, said filling flow curve representing the flow of the molten material from a mold gate through the mold to a selected location in the mold.

4. The method according to claim 3, wherein step (f) is performed by selecting a first starting point within a first element associated with a first equitime curve having a first linear segment; determine points of intersection on boundary lines of adjacent second and third elements by extending a normal line through said first point and perpendicular to said first linear segment; interconnecting the intersection points; and repeating said determining step with each intersection point as a starting point until a point of intersection corresponds to the location of the mold gate.

5. The method according to claim 4, wherein step (f) is further performed by locating crossover points between the filling flow curve and the equitime curves; measuring individual mean linear distances between adjacent pairs of cross-over points; and determining individual filling speeds from the individual means linear distances and the time intervals.

6. The method according to claim 3, wherein step (f) is performed by determining each area bounded between each adjacent pair of equitime curves; determining each means length of individual equitime curves; determining individual mean linear distances between each adjacent pair of equitime curves as a function of each area and each mean length; and determining individual filling speeds from the individual mean linear distances and the time intervals.

7. The method according to claim 3, wherein step (f) is further performed by selecting a first gate point in a first element associated with a first equitime curve having a first linear segment; selecting a second point in a second element associated with a second equitime curve having a second linear segment; interconnecting the first and second points; determining a point of intersection with a third element by extending a normal line through said second point and perpendicular to said first segment; and repeating said determining step with each intersection point as a starting point until a point on the superimposed patterns corresponds to said selected location in the mold.

8. The method according to claim 3, wherein step (f) is further performed by selecting a first starting point on a first linear segment of a first equitime curve; extending a first normal line through said first point and perpendicular to an adjacent second linear segment of a second equitime curve; extending a second normal line through said first point and perpendicular to said first linear segment; determining a second point of intersection on the second equitime curve by extending a bisecting line that bisects the angle included between said first and second normal lines; interconnecting the first and second points; and repeating said extending steps with each point of intersection as a starting point until a point on the superimposed patterns corresponds to said selected location in the mold.

9. The method according to claim 1; and further comprising the step of visually displaying, simultaneously with step (g), a profile of input filling speed settings for the mold over the fill cycle.

10. The method according to claim 1; and further comprising the step of visually displaying, simultaneously with step (g), wall thickness variations at all the elements over the fill cycle.

11. The method according to claim 1; and further comprising the step of visually displaying, simultaneously with step (g), temperature settings of mold plates at all the elements over the fill cycle.

* * * * *